United States Patent
Vermaas

(12) 
(10) Patent No.: US 6,310,200 B1
(45) Date of Patent: Oct. 30, 2001

(54) PROCESS FOR SELECTIVE OXIDATION OF PRIMARY ALCOHOLS OF OLIGOSACCHARIDES

(75) Inventor: Dirk Jan Vermaas, Oss (NL)

(73) Assignee: Akzo Nobel N.V. (NL)

( * ) Notice: Subject to any disclaimer, the term of this patent is extended or adjusted under 35 U.S.C. 154(b) by 0 days.

(21) Appl. No.: 09/357,502

(22) Filed: Jul. 20, 1999

(30) Foreign Application Priority Data

Aug. 13, 1998 (EP) ........................................ 982027

(51) Int. Cl.[7] .................................................. C07H 7/033
(52) U.S. Cl. ........................ 536/124; 536/4.1; 536/18.7; 536/55.2; 536/55.3
(58) Field of Search ........................ 536/4.1, 124, 18.7, 536/55.2, 55.3

(56) References Cited

U.S. PATENT DOCUMENTS 5,338,461   8/1994   Jones ..................................... 210/755

FOREIGN PATENT DOCUMENTS

| 0 775 684 A | 5/1997 | (EP) . |
| 2 742 755 A | 6/1997 | (FR) . |
| WO 95 073030A | 3/1995 | (WO) . |

OTHER PUBLICATIONS de Nooy, A. E. J. et al "Highly selective nitroxyl radical-mediated oxidation of primary alcohol groups in water-soluble glucans" Carbohyd. Res. vol. 268 pp. 89–98, 1995.*
Chang, P. S. et al "Oxidation of the primary alcohol groups of cyclomaltodextrins . . . " Carbohyd. Lett. vol. 3 No. 1, 1pp. 31–38 1998.*

* cited by examiner

Primary Examiner—Kathleen Kahler Fonda
Assistant Examiner—Leigh C. Maier
(74) Attorney, Agent, or Firm—Jeffrey Ihnen

(57) ABSTRACT

The invention relates to a process for the selective oxidation of primary alcohols of oligosaccharides to form the corresponding carboxylic acid derivatives of the alcohols using catalytic amounts of a di-tertiary-alkyl nitroxyl free radical, characterized in that 1,3-dibromo-5,5-dimethylhydantoin or 1,3-dichoro-5,5-dimethylbydantoin is used as oxidant and the reaction is performed in neutral to basic conditions at a pH<10. The process of the invention is useful for the production of (partially protected) oligosaccharides comprising carboxylate groups, both intermediates and end products.

10 Claims, No Drawings

PROCESS FOR SELECTIVE OXIDATION OF PRIMARY ALCOHOLS OF OLIGOSACCHARIDES

FIELD OF THE INVENTION

The invention relates to a new process for selective oxidation of primary alcohols of oligosaccharides.

BACKGROUND OF THE INVENTION

Oligo- and polysaccharides containing uronic acid building blocks such as the glycosaminoglycans heparin, heparan sulfate, chondroitin sulfate and dermatan sulfate have important physiological functions, for instance they may have antithrombotic activity. Such compounds may be isolated from biological sources such as intestinal mucosa, but may also be prepared synthetically.

This generally requires a multi-step synthesis. A key step in this synthesis is the oxidation of primary hydroxyl groups of (intermediate) oligosaccharides to carboxylic acids without affecting either the unprotected secondary hydroxyl groups or the protection of other hydroxyl groups also present in the molecule.

In most methods known in the art for the oxidation of oligosaccharides, such as chromium based oxidation reactions, selective oxidation of the primary hydroxyl groups is not possible. Those reactions require also protection of the secondary hydroxyl groups, which would otherwise be left unprotected. As a result, the selective oxidation of primary hydroxyl groups of oligosaccharides using those known methods needs more than one reaction step (involving protection of the secondary hydroxyl groups, oxidation of the primary hydroxyl groups, and deprotection of the secondary hydroxyl groups).

However, Davis, N. J. and Flitsch, S. L. (*Tetrahedron Letters*, Vol.34, 1181–1184 (1993)) describe a one-step process of selective oxidation of primary hydroxyl groups of partially protected monosaccharides to their carboxylic acids. The reaction is performed in a two-phase solvent system (dichloromethane and water) using sodium hypochlorite as the oxidant in the presence of catalytic amounts of 2,2,6,6-tetramethyl-1-piperidinyloxy (TEMPO). A serious drawback of this process is that it has been found not to be suitable for oligosaccharides comprising more than one saccharide unit. In such cases the oxidation does not fully proceed to form the desired carboxylic acids. Further, a synthetic disadvantage is the two-phase solvent system which requires a phase transfer catalyst.

Also another process for the complete and selective oxidation of primary alcohols of oligo- and polysaccharides was reported (WO 95/07303). However, this process is only successful with unprotected oligosaccharides. For the oxidation also a hypohalite is used and a catalytic amount of a di-tertiary-alkyl nitroxyl, however in an aqueous medium at pH of 9–13. This latter process is unfavourable for the oxidation of protected oligosaccharides, since the protection does not remain intact under these highly basic conditions. Further, large amounts of salts are formed in this reaction, the removal of which is in particular a problem in the case of smaller oligosaccharides (see e.g. De Nooy, A. E. J et al. in *Receuil des Travaux Chimiques des Pays Bas*, 113/03, March 1994).

SUMMARY OF THE INVENTION

A new process has now been found, useful for the selective oxidation of primary hydroxyl groups of oligosaccharides, which does not have the drawbacks mentioned above. The invention relates to a process for the selective oxidation of primary alcohols of oligosaccharides to form the corresponding carboxylic acid derivatives of the alcohols using catalytic amounts of a di-tertiary-alkyl nitroxyl free radical, characterized in that 1,3-dibromo-5,5-dimethylhydantoin or 1,3-dichloro-5,5-dimethylhydantoin is used as oxidant and the reaction is performed in neutral to basic conditions at a pH<10. The process is particularly useful for the selective oxidation of partially protected oligosaccharides.

The process of the invention leads to the production of carboxylic acids of (partially protected) oligosaccharides in good to high yields.

These results are unexpected. Although 1,3-dibromo-5,5-dimethylhydantoin (dibromantin)—and likewise its analogue—is known as a useful oxidizing agent, it is used for both primary and secondary alcohols, but most effectively for secondary alcohols. The oxidation leads to form the corresponding aldehydes and ketones (see e.g. Orazi, O. O. et al., *Anales Asoc.Quim. Argentina* 42, 139–46 (1954) and Reed, R. A. *Chem.Prods*. 23, 299–302 (1960)). Complete and selective oxidation of primary hydroxyl functions using this agent to form the corresponding carboxylic acids was never reported.

Similar results, i.e. the oxidation of primary and secondary alcohols to aldehydes and ketones, were obtained using certain organic N-chloro compounds in the presence of a di-tertiary-alkyl nitroxyl (EP 0,775,684).

Some organic N-halo agents have further been suggested in the preparation of polymeric carboxylates (DE 4209869).

DESCRIPTION OF THE INVENTION

The processes of the present invention is useful for the selective oxidation of primary alcohol functions in oligosaccharides, in particular wherein the hydroxy groups are partially protected. The process of the present invention leaves the protective groups unaffected, so that those groups can be removed at a later stage, when further conversion of the oligosaccharide is required. Preferred oligosaccharides comprise 1–6, and most preferably 1–2, monosaccharide units. Further preferred oligosaccharides are (intermediates in the synthesis of) antithrombotic glycosaminoglycans or glycosaminoglycan-like molecules, such as described in EP 84,999, EP 301,618, EP 454,220, EP 529,715, and the like. In particular preferred are the processes of the invention in which respectively methyl 6-O-acetyl-4-O-[2-O-acetyl-3-O-(phenylmethyl)-α-L-idopyranuronosyl)-2-deoxy-2-[[(phenylmethoxy)carbonyl]amino]-3-O-(phenylmethyl)-α-D-glucopyranoside, 3-O-acetyl-1,6-anhydro-2-azido-2-deoxy-4-O-[2,3-bis-O-(phenylmethyl)-β-D-glucopyranuronosyl]-β-D-glucopyranose, methyl 4-O-(2,3-bis-O-methyl-α-L-idopyranuronosyl)-2,3,6-tris-O-phenylmethyl)-β-D-glucopyranose and methyl 4-O-(2,3-bis-O-methyl-β-D-glucopyranuronosyl)-2,3,6-tris-O-(phenylmethyl)-β-D-glucopyranose are formed. The oxidation of the protected oligosaccharides is preferably performed at a pH of 7–9, and most preferably at pH is 8.

The di-tertiary-alkyl nitroxyl free radical may be acyclic, but is preferably a cyclic compound, as described in WO 95/07303 and EP 0,775,684. These cyclic compounds have the formula:

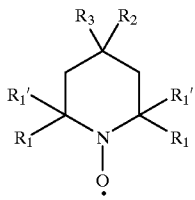

wherein $R_1$ and $R_1'$ are independently lower alkyl; $R_2$ and $R_3$ are both hydrogen or are both lower alkoxy, or one is hydrogen and the other is hydroxy, lower alkoxy, lower alkylcarbonyloxy, lower alkylcarbonylamino or arylcarbonyloxy, or $R_2$ and $R_3$ together are a ketal group of formula a–c:

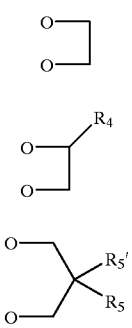

wherein $R_4$ is lower alkyl; and $R_5$ and $R_5'$ are independently hydrogen or lower alkyl. The most preferred nitroxyl compound is 2,2,6,6,-tetramethyl-piperidin-1-oxyl. In the process of the invention, a catalytic amount of a nitroxyl compound is used. The person skilled in the art will understand what is meant herewith. Preferably, a catalytic amount of nitroxyl is 0.05–10 mol %, and in particular 0.5–5 mol %, and most preferably 1–3 mol % based on the alcohol.

A preferred process according to the invention is the process in which 1,3-dibromo-5,5-dimethylhydantoin is used as the oxidant.

The oxidant is used in at least stoichiometric amounts based on the alcohol. Preferably, 2–4 mol. equivalents of the active halogen (i.e. (halogen)$^+$) is used, which means in the case of dibromantin 1–2 mol. equivalents of the compound.

In a suitable process according to the invention, the nitroxyl compound may be added to a solution of the alcohol in an appropriate solvent, at controlled pH, after which the oxidant may be added. However, the reaction sequence is not critical, the reagents may also be contacted with each other in another sequence.

The reaction may be performed in a variety of different solvents which preferably are miscible with water. Preferred solvents are tetrahydrofuran, tert.-butanol and acetonitril, of which tert.-butanol is most preferred.

The pH of the reaction mixture is controlled using procedures well known in the art. A very suitable method is buffering with a sodium hydrogen carbonate solution.

The reaction temperature is not very critical, but is preferably 0° C. to 30° C., and most preferably room temperature.

Protective groups which are present in the oligosaccharides in the process of the invention, are well known in the art. Preferred protective groups include benzyl, benzoyl and acetyl for hydroxy groups, and benzyl and methyl for the carboxylate groups of uronic acids. Other protective groups, such as levoluyl, alkoxyphenyl, chloroacetyl, trityl, and the like may be used with equal success. The anomeric center may be protected by an alkyl group or by means of a 1,6-anhydro functionality.

Benzyloxycarbonyl, benzoyl and azide are useful groups to protect amino functions.

The invention is further illustrated by the following examples, which does not mean any limitation.

EXAMPLES

Abbreviations used:

Bzl=benzyl

Z=benzyloxycarbonyl

Example 1

Synthesis of methyl 6-O-acetyl-4-O-[2-O-acetyl-3-O-(phenylmethyl)-α-L-idopyranuronosyl)2-deoxy-2-[[(phenylmethoxy)carbonyl]amino]-3-O-(phenylmethyl)-α-D-glucopyranoside

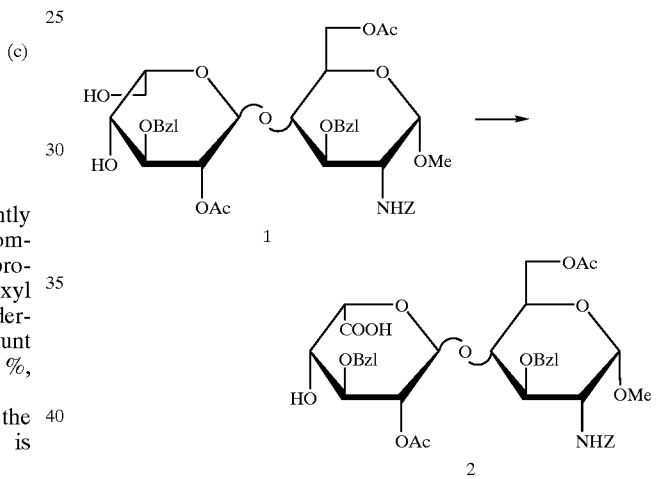

10 g of methyl 6-O-acetyl-4-O-[2-O-acetyl-3-O-(phenylmethyl)-α-L-idopyranosyl)-2-deoxy-2-[[(phenylmethoxy)carbonyl]amino]-3-O-(phenylmethyl)-α-D-glucopyranoside (1) was dissolved in 90 ml of t-butanol and the solution was cooled at 10° C. Successively the following reagents were added: 26 ml of water, 4,65 g of sodium hydrogencarbonate, 44 mg of 2,2,6,6-tetramethyl-1-piperidinyloxy free radical and 5,85 g of 1,3-dibromo-5,5-dimethylhydantoin. The mixture was stirred for 6 hours at 20° C. The reaction was queched with 2,85 g of sodium thiosulphate in 10 ml of water at 10° C. and the product was isolated by extraction and evaporation.

The yield of the title compound (2) was 8,4 g.

TLC: dichloromethane, methanol 90/10 on silica, $R_f$=0.2.

Further identification: $^{13}$C-NMR of methyl 6-O-acetyl-4-O-[2-O-acetyl-6-methyl-3-O-(phenylmethyl)-α-L-idopyranuronosyl]-2-deoxy-2-[[(phenylmethoxy)carbonyl]amino]-3-O-(phenylmethyl)-α-D-glucopyranoside (methyl ester of 2, prepared from 2 according to generally known methods. Solvent was CDCl$_3$ and chemical shifts are relative to TMS set at 0 ppm):

| position | C1 | C2 | C3 | C4 | C5 | C6 |
|---|---|---|---|---|---|---|
| glucuronamide unit | 98.9 | 54.6 | 79.1 | 75.1 | 69.2 | 62.3 |
| iduronic acid unit | 98.1 | 67.1 | 74.4 | 67.7 | 68.4 | 170.7 |

Example 2

Synthesis of methyl 2,3-bis-O-(phenylmethyl)-β-D-glucopyranosiduronic acid

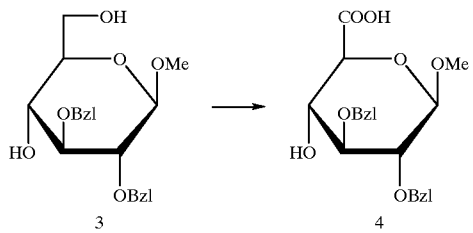

A solution of 50 mg of methyl-2,3-O-(phenylmethyl)-β-D-glucopyranoside (3) in 0.88 ml of tetrahydrofuran and 0.22 ml of water was prepared. Successively the following reagents were added: 67.6 mg of sodium hydrogencarbonate, 0.36 mg of 2,2,6,6-tetramethyl-1-piperidinyloxy free radical and 65.8 mg of 1,3-dibromo-5,5-dimethylhydantoin. The mixture was stirred and checked with TLC. Upon completion, the reaction was queched with 0.89 ml of saturated sodium hydrogencarbonate solution and 0,26 ml 10% sodium thiosulphate solution and the product was isolated by extraction and evaporation.

The product was purified by column chromatography. The yield of the title compound (4) was: 48 mg.
TLC: dichloromethane, methanol 90/10 on silica, $R_f$=0.2.
Further identification: $^1$H-NMR of methyl 2,3-bis-O-(phenylmethyl)-6-(phenylmethyl)-β-D-glucopyranosiduronic acid (benzyl ester of 4, prepared from 4 according to generally known methods. Solvent was $CDCl_3$ and chemical shifts are relative to TMS set at 0 ppm):

| position | δ | multiplicity |
|---|---|---|
| H1 | 4.37 | d |
| H2 | 3.44 | dd |
| H3 | 3.51 | m |
| H4 + H5 | 3.84–3.92 | m |
| OH on C4 | 2.74 | d |
| $CH_2$ from Bzl on C2 and C3 | 4.68–4.91 | m |
| $CH_2$ from Bzl on C6 | 5.25 | s |
| aromatic protons | 7.26–7.38 | m |

The following compounds were all prepared according to the above described methods, starting from the corresponding 6-hydroxy compounds:

| compound | Eluens on TLC (SiO$_2$) | $R_F$ value |
|---|---|---|
| 3-O-acetyl-1,6-anhydro-2-azido-2-deoxy4-O-[2,3-bis-O-(phenylmethyl)-β-D-glucopyranuronosyl]-β-D-glucopyranose | CH$_2$Cl$_2$/MeOH 9/1 | 0.15 |
| methyl 4-O-(2,3-bis-O-methyl-α-L-idopyranuronosyl)-2,3,6-tris-O-phenylmethyl)-β-D-glucopyranose | CH$_2$Cl$_2$/MeOH 9/1 | 0.30 |
| methyl 4-O-(2,3-bis-O-methyl-β-D-glucopyranuronosyl)-2,3,6-tris-O-(phenylmethyl)-β-D-glucopyranose | CH$_2$Cl$_2$/MeOH 9/1 | 0.40 |
| methyl 4-O-(2-O-acetyl-3-O-methyl-α-L-idopyranuronosyl)-2,3,6-tris-O-(phenylmethyl)-β-D-glucopyranose | CH$_2$Cl$_2$/MeOH 9/1 | 0.20 |
| methyl 4-O-(2-O-acetyl-3-O-methyl-α-L-idopyranuronosyl)-3-O-methyl-2,6-bis-O-(phenylmethyl)-β-D-glucopyranose | CH$_2$Cl$_2$/MeOH 9/1 | 0.10 |
| methyl 4-O-(2,3-bis-O-methyl-α-L-idopyranuronosyl)-3,6-bis-O-methyl-2-O-(phenylmethyl)-β-D-glucopyranose | CH$_2$Cl$_2$/MeOH 9/1 | 0.10 |
| methyl 4-O-(2,3-bis-O-methyl-α-L-idopyranuronosyl)-6-O-methyl-2,3-bis O-(phenylmethyl)-β-D-glucopyranose | CH$_2$Cl$_2$/MeOH 85/15 | 0.60 |
| methyl 6-O-acetyl-4-O-[2-O-acetyl-3-O-(phenylmethyl)-α-L-idopyranuronosyl]-2-O-(benzoylamino)-2-deoxy-3-O-(phenylmethyl)-β-D-glucopyranose | CH$_2$Cl$_2$/MeOH 9/1 | 0.35 |
| methyl 4-O-(2,3-bis-O-methyl-β-D-glucopyranuronosyl)-6-O-methyl-2,3-bis-O-(phenylmethyl)-β-D-glucopyranose | CH$_2$C$_2$/MeOH 9/1 | 0.30 |
| 1,6-anhydro-2,3-bis-O-[2-(1,1-dimethylethoxy)-2-oxoethyl]4-O-(2,3-bis-O-methyl-β-D-glucopyranuronosyl)-β-D-glucopyranose | CH$_2$Cl$_2$/MeOH 95/5 | 0.10 |
| methyl 2-O-[2-(1,1-dimethylethoxy)-2-oxoethyl]-4-O-(2,3-bis-O-methyl-α L-idopyranuronosyl)-6-O-methyl-3-O-(phenylmethyl)-β-D-glucopyranose | CH$_2$Cl$_2$/MeOH 9/1 | 0.40 |
| methyl 4-O-(2,3-bis-O-methyl-α-L-idopyranuronosyl)-6-[[2-oxo-2-(phenylmethoxy)ethyl][phenylmethoxy)carbonyl]amino]-2,3-bis-O-(phenylmethyl)-β-D-glucopyranose | CH$_2$Cl$_2$/MeOH 9/1 | 0.40 |
| methyl 4-O-[2-O-acetyl-3-O-(phenylmethyl)-α-L-idopyranuronosyl]-6-O-benzoyl-2-deoxy-2-[[(phenylmethoxy)carbonyl]amino]-3-O-(phenylmethyl)-α-D-glucopyranoside | toluene/ acetone 6/4 | 0.10 |
| methyl 4-O-[2-O-benzoyl-3-O-(phenylmethyl)-α-L-idopyranuronosyl]-6-O benzoyl-2-deoxy-2-[[(phenylmethoxy)carbonyl]amino]-3-O-(phenylmethyl)-α-D-glucopyranoside | CH$_2$Cl$_2$/MeOH 9/1 | 0.60 |
| methyl 4-O-(2-O-acetyl-3-O-methyl-α-L-idopyranuronosyl)-3,6-bis-O-methyl-2-O-(phenylmethyl)-β-D-glucopyranose | CH$_2$Cl$_2$/MeOH 9/1 | 0.20 |
| methyl [3-O-(phenylmethyl)-α-L-idopyranosyluronic acid 2,6-δ-lactone]-(1→4)-O-[6-O-acetyl-2-deoxy-3-O-(phenylmethyl)-2-[[(phenylmethoxy)carbonyl]amino]-α-D-glucopyranoside] | ether/heptane 9/1 | 0.40 |
| methyl [3-O-(phenylmethyl)-α-L-idopyranosyluronic acid 2,6-δ-lactone]-(1→4)-O-[2-deoxy-3,6-bis-O-(phenylmethyl)-2- | ether/heptane 8/2 | 0.40 |

-continued

| compound | Eluens on TLC (SiO$_2$) | R$_F$ value |
| --- | --- | --- |
| [[(phenylmethoxy)carbonyl]amino]-α-D-glucopyranoside] 17-azido-3,6,9,12,15-pentaoxaheptadecyl[2,6-bis-O-ethyl-3,4-O-(1-methylethylidene)-β-D-galactopyranosyl]-(1→4)-O-(3-O-ethyl-α-L-idopyranosyluronic acid 2,6-δ-lactone)-(1→3)-(2,6-bis-O-ethyl-β-D-galactopyranosyl)-(1→4)-O-(3-O-ethyl-α-L-idopyranosyluronic acid 2,6-δ-lactone) | CH$_2$Cl$_2$/MeOH 9/1 | 0.90 |

What is claimed is:

1. A process for the selective oxidation of primary alcohols of oligosaccharides to form the corresponding carboxylic acid derivatives of the alcohols using catalytic amounts of a di-tertiary-alkyl nitroxyl free radical, comprising reacting an oligosaccharide comprising at least one primary hydroxyl group with an oxidant selected from 1,3-dibromo-5,5-dimethylhydantoin and 1,3-dichloro-5,5-dimethylhydantoin in the presence of catalytic amounts of the di-tertiary-alkyl nitroxyl free radical in neutral to basic conditions at a pH<10.

2. The process of claim 1, wherein the oligosaccharide is partially protected.

3. The process of claim 1, wherein the oligosaccharide is an intermediate in the synthesis of glycosaminoglycans or glycosaminoglycan-like molecules.

4. The process of claim 1, wherein the pH is 7–9.

5. The process of claim 1, wherein the di-tertiary-alkyl nitroxyl free radical is 2,2,6,6-tetramethyl-1-piperidinyloxy.

6. The process of claim 1, wherein the oxidant is 1,3-dibromo-5,5-dimethylhydantoin.

7. The process of claim 1, wherein the molar ratio of the primary alcohol to the oxidant is 1:1 to 1:2.

8. The process of claim 1, wherein the reaction temperature is 0°C. to 30° C.

9. The process of claim 1, wherein the oligosaccharide is a glycosaminoglycan or a glycosaminoglycan-like molecule.

10. The process of claim 2, wherein the oligosaccharide is a glycosaminoglycan or a glycosaminoglycan-like molecule.

* * * * *